United States Patent [19]

Chu

[11] Patent Number: 4,597,398
[45] Date of Patent: Jul. 1, 1986

[54] ORAL HYGIENE INSTRUMENT FOR USE WITH ORTHODONTIAL APPLIANCES AND METHOD OF CLEANING SAME

[76] Inventor: Grace M. M. Chu, 2227 Foreland, Houston, Tex. 77077

[21] Appl. No.: 702,246

[22] Filed: Feb. 15, 1985

[51] Int. Cl.$^4$ ............................................. A61C 15/00
[52] U.S. Cl. ................................. 132/92 R; 132/91; 433/3
[58] Field of Search .................. 433/3; 132/91, 92 R, 132/92 A

[56] References Cited

U.S. PATENT DOCUMENTS

| | | | |
|---|---|---|---|
| 1,608,212 | 11/1926 | Hochstadter | 132/92 R |
| 1,780,045 | 10/1930 | Schubert | 132/92 R |
| 2,451,849 | 10/1948 | Massimiano | 132/92 R |
| 2,724,390 | 11/1955 | Sokoloski | 132/92 R |
| 3,799,177 | 3/1974 | Bragg | 132/92 R |
| 3,881,502 | 6/1975 | Bennington | 132/91 |
| 3,885,579 | 5/1975 | Navrat | 132/92 R |
| 3,924,647 | 12/1975 | Lindblad | 132/92 R |
| 4,005,722 | 2/1977 | Bragg | 132/92 R |
| 4,031,909 | 6/1977 | Kelley | 132/91 |
| 4,434,807 | 3/1984 | Huskey | 132/92 A |

FOREIGN PATENT DOCUMENTS 2074876  11/1981  United Kingdom ............. 132/92 A

*Primary Examiner*—John J. Wilson
*Attorney, Agent, or Firm*—Carwell & Helmreich

[57] ABSTRACT

An instrument for promoting oral hygiene particularly with patients having orthodontial appliances. An elongate handle includes a short hollow post at the distal end thereof disposed generally transverse to the handle. Flossing material is threaded through and out the post. In operation, the post is disposed by means of the handle between the orthodontial band and adjacent the spacing between teeth which are desired to be cleaned. The floss protruding out the post is then forced between the spacing to effect flossing thereof.

21 Claims, 6 Drawing Figures

U.S. Patent   Jul. 1, 1986   4,597,398
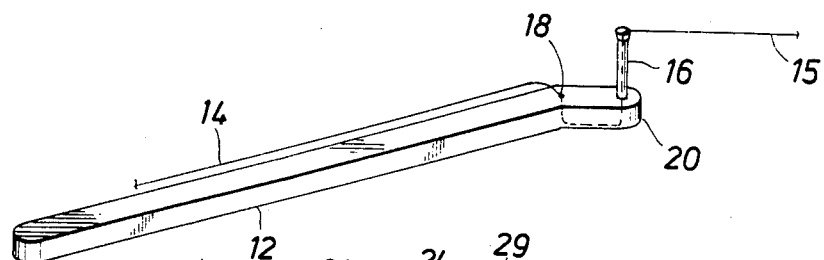
FIG.1
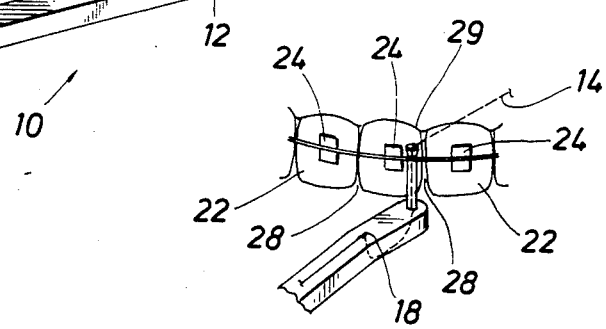
FIG.2
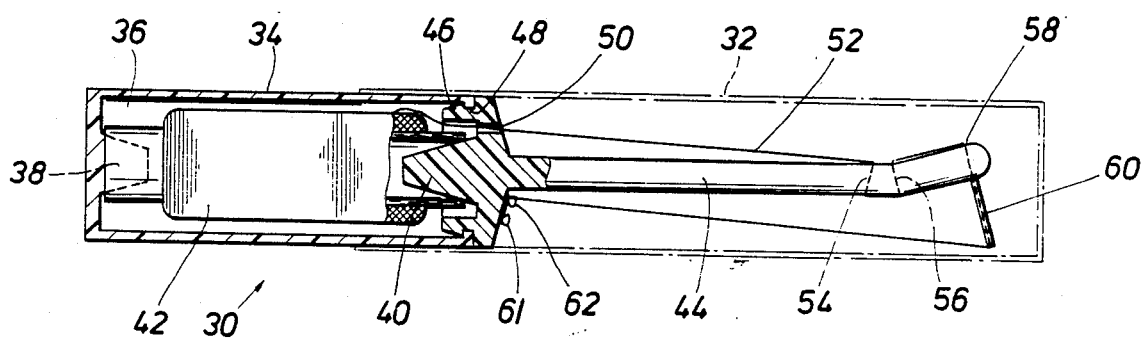
FIG.3
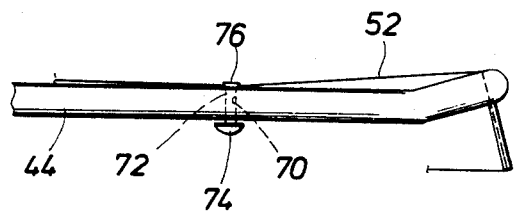
FIG.4
FIG.5
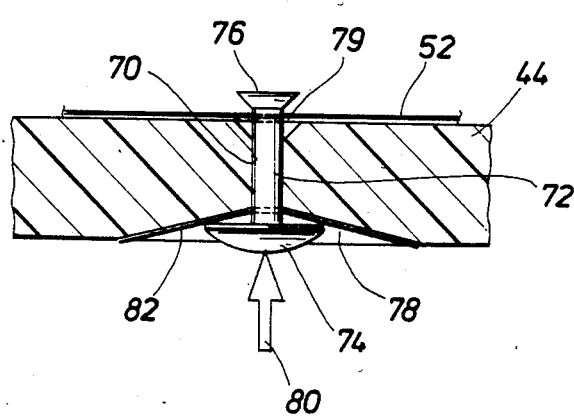
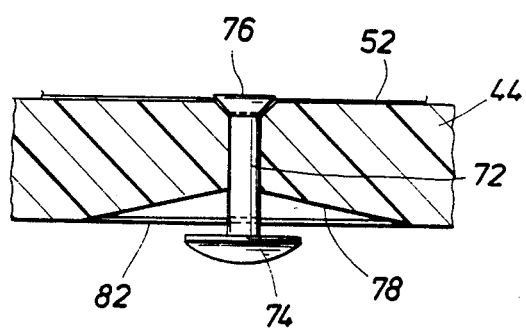
FIG.6

ORAL HYGIENE INSTRUMENT FOR USE WITH ORTHODONTIAL APPLIANCES AND METHOD OF CLEANING SAME

BACKGROUND OF THE INVENTION

In the field of oral hygiene, the benefits of regular cleaning of the teeth by means of flossing or the like have been known for some time. Accordingly, numerous instruments have been devised for facilitating cleaning between the teeth and gum lines by means of routing an appropriate dental floss tape, thread, or other members between the teeth. Such apparatus have included, for example, fork-like instruments for supporting a length of floss of perhaps one inch, such support being semi-rigid much in the manner in which a manual digital flossing is effected to force the flossing material between the teeth. Yet another example of such apparatus is depicted in U.S. Pat. No. 4,011,658 to Tarrson. This device has the major disadvantage of requiring tedious repeated insertions between each tooth. These apparatus have met with varying degrees of success and have even included features such as being combined with a toothbrush, means for providing a reservoir of such floss in conjunction with the instrument for ready use, and the like.

However, one area of application of such devices which has been sorely neglected has been instances wherein various orthodontial appliances such as braces and the like have been applied to the teeth, rendering flossing either in a conventional manner or with use of the aforementioned appliances extremely difficult. In the case of forked instruments, this even becomes virtually impossible. The problem has been of a growing proportion with the increased public awareness of the need for dental care and the resultant increased frequency of application of such orthodontial appliances. Moreover, the need to floss is even greater amongst people having such orthodontial appliances. The primary difficulty presented by these appliances in an attempt to perform an effective flossing operation results from the particular structure of the common form of these appliances. More particularly, it is conventional practice to provide a plurality of metallic bands about the teeth. A wire is then strung through the bands adjacent the outer surfaces of the teeth and tensioned so as to correct the teeth alignment as desired. However, due to the presence of these wires extending adjacent to and about the outer periphery of the outer surfaces of the teeth, it is difficult if not impossible to interject a length of floss between the teeth inasmuch as the wires prevent movement of the floss transverse thereto down to the gum line where flossing is particularly important.

Thus, a method was highly desired for effecting a facile flossing of teeth wherein the aforesaid orthodontial appliances had been applied, as well as a simple but effective instrument for effecting such flossing. These and other objectives have been accomplished with the teachings of the present invention.

SUMMARY OF THE INVENTION

An instrument for promoting oral hygiene particularly with patients having orthodontial appliances. An elongate handle includes a short hollow post at the distal end thereof disposed generally transverse to the handle. Flossing material is threaded through and out the post. In operation, the post is disposed by means of the handle between the orthodontial band and adjacent the spacing between teeth which are desired to be cleaned. The floss protruding out the post is thence forced between the spacing to effect flossing thereof.

In a preferred embodiment, the handle is further provided with two apertures extending transversely therethrough, a first in coaxial alignment with the post and a second being substantialy parallel and adjacent thereto. Floss is routed from one side of the handle through the second aperture, thence along the opposite side of the handle, through the first aperture, and thence through and out the post. The purpose of the routing and the apertures is to provide friction between the floss and the handle. In this manner, tension may be applied to the portion of the floss extending outwards of the post for flossing purposes (wherein substantial force is often required to force the floss between the teeth), thus preventing floss from simply being pulled out through the apertures and post during the flossing operation.

BRIEF DESCRIPTION OF THE DRAWINGS

FIG. 1 is a pictorial view of an embodiment of the oral hygiene instrument of the present invention.

FIG. 2 is a pictorial view of a portion of the embodiment of the invention depicted in FIG. 1 in use.

FIG. 3 is a side view partially in section of an alternate embodiment of the oral hygiene instrument of the present invention.

FIG. 4 is a pictorial side view of a portion of an embodiment of the present invention.

FIG. 5 is a side view in section of a portion of FIG. 4.

FIG. 6 is another side view in section of a portion of the invention depicted in FIG. 4.

DETAILED DESCRIPTION OF THE INVENTION

Referring first to FIG. 1, there will be seen depicted therein generally an oral hygiene instrument 10 of the present invention comprised generally of an elongate handle 12, a length of floss 14, and a short hollow post 16 of a nominal length of 13 mm at the distal end of the handle and extending away therefrom generally transverse or normal to the handle 12. The post 16 is preferably 0.5 mm in diameter. In the embodiment depicted in FIG. 1, apertures 18 and 20 are provided at the distal end of the handle 12 through which the floss is routed. A close examination of FIG. 1 will reveal that in the embodiment depicted therein the aperture 20 is preferably aligned in a coaxial alignment with the post 16, which has an aperture extending therethrough whereby the floss 14 may be routed through aperture 20 and post 16 and outwards thereof.

Referring now to FIG. 2, the embodiment of the invention depicted in FIG. 1 may be seen in a typical application in conjunction with a patient having orthodontial appliances on their teeth. Thus, it will be noted that the teeth 22 will each generally have some form of a band 24 or spacer disposed thereabout through which is routed a length of wire 26. Upon tensioning of the wire 26 the teeth 22 will be brought into alignment as desired and as well known in the orthodontial arts. However, as aforementioned in the Background, it will be readily apparent from FIG. 2 that heretofore it has been extremely difficult to dispose a length of flossing material between the spaces 28 between the teeth so as to perform an effective flossing operation between the teeth and particularly downwards adjacent the gum line 29. The reason for this difficulty is due to the obstructing effect of the wire 26 preventing movement of the flossing material between the teeth downwards adjacent the gum line 29. However, as shown clearly in FIG. 2, with the present invention, the post 16 of the instrument 10 may be inserted between the wire 26 and the area to be flossed such as the spaces 28 between the teeth and supported there by the handle 12 by one hand. The floss 14 is thereafter grasped by the other hand digitally inside the mouth at a location radially inwards of the teeth so as to force the floss 14 protruding from the tip of the post 16 between the spaces 28 in the teeth and toward the gum line as desired. In operation, it will be appreciated that the floss 14 may be held against the handle 12 by one hand, and the opposite end 15 of the floss held by the fingers of the other hand, so as to effect the flossing operation. The purpose of the apertures 18 and 20 is to provide additional friction between the floss 14 and the handle 12 so as to prevent floss being pulled at the end 15 through the apertures 18 and 20 and the post 16 during the flossing operation. Accordingly, it will be noted that aperture 18 is preferably not perpendicular relative to handle 12, but rather extends therethrough at an oblique angle to provide friction and prevent pulling of floss therethrough during flossing.

Referring now to FIG. 3, an alternate embodiment 30 of the instrument of the present invention will be seen depicted therein. A generally cylindrically shaped floss container handle 34 defines a cavity 36 having a spindle 38 at one end. At the opposed end of the container 34 a circular retaining ridge 48 is provided. Disposed in coaxial alignment with the container 34 is an elongate neck 44 having a portion at one end defining a spindle 40 and a circular edge 46. When the handle 34 and neck 44 are disposed in coaxial alignment, the edge 46 operates against the ridge 48 in a press-fit so that the handle 34-neck 44 combination act as one integral unit. It will be appreciated from FIG. 3 that when the handle 34 and neck 44 are in such alignment, the spindles 38 and 40 are also in coaxial alignment so as to support a roll of floss 42. A hollow cover 32 may be provided also of a generally cylindrical configuration and having an internal diameter slightly smaller than the outer diameter of the handle 34 so that in a press-fit arrangement, the cover 32 may be removably retained by the handle 34 about the neck 44 for purposes of maintaining the cleanliness of the appliance when stored.

Still referring to FIG. 3, the spindle 40 will preferably include an aperture 50 so that a floss strand 52 may be routed from the floss roll 42 through the aperture 50 and through a third aperture 54 disposed generally adjacent the distal end of the neck 44 and generally transverse to the longitudinal axis of the neck 44 and handle 34. A fourth aperture 56 is also disposed at the distal end of the neck 44 and generally adjacent to aperture 54 and transverse to the longitudinal axis of the neck 44. The floss strand 52, after having been routed through the third aperture 54 will thence be routed along the surface of the neck 44 and back through the fourth aperture 56. A hollow post 60 having a nominal length of ½" is disposed also at the distal end of the neck 44 and extends generally transverse to the neck 44. A fifth aperture 58 is also disposed at the distal end of the neck 44 in coaxial alignment with the aperture extending through the post 60. In this manner, the floss strand 52 may thence be routed from the fourth aperture 56 through the fifth aperture 58 and hollow passageway extending through the post 60 and outwards to a terminating post 62 disposed on the spindle 40. A blade 61 may also be provided extending from the spindle 40 at a location adjacent the terminating post 62. In storage, the floss strand 52 will simply be wrapped about the terminating post as shown in FIG. 3. However, in use, the floss strand 52 will be released from the terminating post 62 and grasped by one hand and extended in a direction generally parallel to the longitudinal axis of neck 44 as shown in FIG. 2. If necesssary, a new length of floss strand 52 is exposed for use by pulling on the floss strand so as to release floss from the floss roll 42, cause it to travel through the aperture 50, and the apertures 54, 56, and 58, respectively, through the post 60, and outwards thereof for use. Upon conclusion of use of the instrument, however, the portion of the floss strand 52 extending outwards of the post 60 will simply be wrapped about the terminator post and thence forced against the blade 61 so as to cut off the used portion of the floss strand 52 for disposal thereof, whereupon the cover 32 is replaced about the handle 34 and the instrument 30 thereafter stored.

With reference now to FIG. 4, an alternate apparatus for providing the desired friction between the floss strand 52 and the instrument 30 is depicted therein. It will be recalled that the purpose of the apertures 54 and 56 is to provide such friction whereby, in use, the floss strand 52 will not be pulled through the apertures when applying the necessary force to position the floss strand 52 between the teeth. In the embodiment depicted in FIG. 4, an apparatus is shown which is intended to replace the apertures 54 and 56 depicted in FIG. 3. More particularly, in the embodiment of FIG. 4, a single aperture 70 is provided extending transversely through the neck 44. Disposed within the aperture 70 is a pin 72 having a flared tail 76 at one end, and a head 74 at the opposed end. The floss strand 52, in being routed from the cavity 36 or any other location adjacent the handle, will preferably be routed through an aperture in pin 72 as shown in FIG. 5. Alternatively, one or two turns of the floss may be made about the pin 72 adjacent the tail 76 prior to being routed through the aperture 58 and post 60.

Reference to FIGS. 5 and 6 will disclose operation of the pin 72 in greater detail. First, with respect to FIG. 5, the pin 72 is depicted in a configuration wherein a new length of floss strand 52 is being pulled through the post 60. In this configuration, the tail 76 is disposed away from the neck 44 so as to permit the floss strand 52 to be pulled in the longitudinal direction of the neck 44. An indent 78 is provided in the handle surface 44 which carries a spring member 82. When the pin 72 is disposed transversely in the handle 44 in the manner just described, the spring 82 will be depressed when the pin 72 is moved in the direction of the arrow 80. However, with reference to FIG. 6, when it is desired to lock the position of the floss strand 52 relative to the neck 44 for storage or use of the instrument 30, the pin 72 is permitted to be returned to the static position depicted in FIG. 6 by means of the spring 82. In this position, it will be noted that the tail 76 of the pin 72 is forcibly retained against the surfaces of an indent 79 on the opposite side of the surface defining the indent 78. In this manner, the tail 76 will be forcibly pressed against the surface defining the second indent 79 so as to retain the flossing strand 52 wrapped thereabout against the surface of the indent 79. In this manner, further extrusion of the floss strand 52 in the longitudinal direction of the handle 44 is thereby prevented.

In one embodiment, the components of the instrument 10 or 30 are preferably fashioned of a plastic material and the post 16 or 60 has a sufficiently thin-wall construction so as to permit slight movement thereof relative to the handle 12 or neck 44 for purposes of safety when disposing the post 16 or 60 between the wires 26 and the teeth 22, e.g., the posts 16 or 60 have a slight amount of "give" relative to the handle 12 or neck 44.

It is therefore apparent that the present invention is one well adapted to obtain all of the advantages and features hereinabove set forth, together with other advantages which will become obvious and apparent from a description of the apparatus itself. It will be understood that certain combinations and subcombinations are of utility and may be employed without reference to other features and subcombinations. Moreover, the foregoing disclosure and description of the invention is only illustrative and explanatory thereof, and the invention admits of various changes in the size, shape and material composition of its components, as well as in the details of the illustrated construction, without departing from the scope and spirit thereof.

What is claimed is:

1. An oral hygiene instrument for use in cleaning between a plurality of teeth having a wire spaced a predetermined distance from the outer surfaces of said teeth and in outwardly-spaced relation thereto, comprising:
   an elongated handle member;
   means interconnected to one end of said handle for inserting between said wire and said teeth, said means comprising a post having a dental floss-receiving aperture extending longitudinally therethrough for supporting one end of a length of said floss at a location between said wire and said teeth, said post having a width less than at least one of said predetermined distances.

2. The apparatus of claim 1, wherein said post means extends transversely from the distal end of said handle means.

3. The apparatus of claim 2, wherein said handle means defines a first aperture extending therethrough in coaxial alignment with said floss-receiving aperture of said post means.

4. The apparatus of claim 3, further including a length of dental floss extending through said apertures in said post means and said handle means.

5. The apparatus of claim 4, further including a second aperture extending transversely through said handle means and adjacent said first aperture.

6. The apparatus of claim 5, wherein said length of said dental floss extends through said second aperture, from said second aperture to said first aperture, and through said first aperture and said aperture in said post means.

7. The apparatus of claim 6, wherein said handle means includes:
   a spindle means having an aperture therethrough;
   a floss container means interconnected to said spindle means;
   a floss roll disposed within said container means; and
   wherein said length of floss extends from said floss roll through said aperture in said spindle means.

8. The apparatus of claim 7, wherein said floss container includes a spindle and wherein said floss roll is carried by said spindle means and said floss container spindle.

9. The apparatus of claim 8, wherein said spindle means includes a terminating post means for securedly anchoring one end of said length of floss.

10. The apparatus of claim 9, wherein said spindle means includes a blade means for cutting said length of floss at a location adjacent said terminating post means.

11. The apparatus of claim 10, further including a cover means extending about said handle means and releasably retained by said container means.

12. The apparatus of claim 4, wherein said handle means further includes:
   an additional aperture extending therethrough in transverse relation to said handle means;
   a pin means retrievably and movably disposed in said additional aperture for alternately preventing and permitting longitudinal movement of said dental floss relative to said handle means as a function of first and second positions of said pin means relative to said handle means; and
   wherein said length of dental floss further extends about said pin means.

13. The apparatus of claim 12, wherein said post means is rigidly attached to said handle means at a first end and has a second end movable relative to said first end.

14. The apparatus of claim 12 further including spring means for biasing said pin means at one of said first or second positions and for returning said pins means to said one of said first and second positions from a remaining one of said first and second positions.

15. The apparatus of claim 1, wherein said post means has a length of about ½ inch.

16. An instrument for performing oral hygiene operations on teeth having a wire spaced a predetermined distance outwards from the outer surface of said teeth, comprising:
   an elongate handle member;
   means on said handle for inserting between said wire and said teeth, said means comprising a post interconnected to one end of said handle member and forming an angle with said handle member, said post having a width less than said predetermined distance; and
   means for supporting one end of a length of dental floss from one end of said post member.

17. The apparatus of claim 16, wherein a portion of said length of dental floss extends through said post member.

18. The apparatus of claim 17, further including friction means for preventing movement of said portion of said length of said dental floss through and away from said post member.

19. The apparatus of claim 18, wherein said friction means comprises at least one aperture extending through said handle member and having extending therethrough a portion of said length of said dental floss.

20. The apparatus of claim 16, wherein said post member is substantially perpendicular to said handle member.

21. A method for cleaning space between teeth circumscribed by a wire band extending from a gum line, comprising:
   supporting a first end of a length of dental floss from a first location between said band and said space adjacent said gum line;
   supporting a second end of said length of dental floss from a second location inwards of said band and said space; and
   moving said second end from said second location whereby a portion of said length of floss moves through said space.

* * * * *